United States Patent [19]

Munson, Jr. et al.

[11] Patent Number: 5,190,953
[45] Date of Patent: Mar. 2, 1993

[54] HETEROCYCLIC CARBOXYLIC ACID AMIDES AND ESTERS OF AZABICYCLIC COMPOUNDS AS GASTRIC PROKINETIC, ANTIEMETIC, ANXIOLYTIC AND ANTIARRHYTHMIC AGENTS

[75] Inventors: Harry R. Munson, Jr., Leawood, Kans.; Gunnar E. Jagdmann, Apex, N.C.

[73] Assignee: A. H. Robins Company, Incorporated, Richmond, Va.

[21] Appl. No.: 858,259

[22] Filed: Mar. 26, 1992

[51] Int. Cl.$^5$ .................. A61K 31/435; C07D 471/08
[52] U.S. Cl. .................................... 514/299; 546/112
[58] Field of Search ........................ 546/112; 514/299

[56] References Cited

U.S. PATENT DOCUMENTS

| | | | |
|---|---|---|---|
| 4,213,983 | 7/1990 | Hadley | 424/250 |
| 4,593,034 | 6/1986 | Munson | 514/305 |
| 4,612,319 | 9/1986 | King | 514/305 |
| 4,826,839 | 5/1989 | King | 514/214 |
| 4,983,600 | 1/1991 | Ward | 415/214 |
| 5,091,397 | 2/1992 | Wadsworth | 514/359 |
| 5,110,828 | 5/1992 | Bromige | 514/413 |

FOREIGN PATENT DOCUMENTS 0202062 11/1986 European Pat. Off. .

OTHER PUBLICATIONS

Grob and Rank, Helv. Chim. Acta. 37, 1681-88 (1954).
Fischer and Grob, Helv. Chim. Acta. 51, 153-63 (1968).
Barnes et al. Nature 338, 762-3 (1989).
Pavia, Ann. Repts. Med. Chem. 25, 21 (1989).
Barnes et al., J. Pharm. Pharmacol. 1988, 40:668.
Kilpatrick et al., Nature 330, 24/31, Dec. 1987.
Costall et al., Pharm. Ther. 47, 181-02 (1990).
Kidd et al., Eur. J. Pharm., 211, 133-36 (1992).
Wise and Heffner, Ann. Repts. Med. Chem. 26, 53-62.
Audia and Cohen, Ann. Repts. Med. Chem. 26, 103-112.
Robertson and Fuller, Ann. Repts. Med. Chem. 23, 49-58.
Johnson, Ann. Repts. Med. Chem. 22, 41-50.

Primary Examiner—Bernard Dentz
Attorney, Agent, or Firm—R. F. Boswell, Jr.

[57] ABSTRACT

Novel 1-azabicyclo[3.2.1]octan-5-ylmethyl and 1-azabicyclo[3.3.1]nonan-5-ylmethyl amines and alcohols are coupled with aryl carboxylic acids to obtain compounds having the formula:

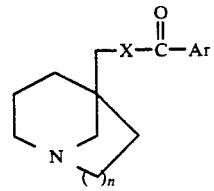

wherein X is —O— or —NH— and n is 1 or 2 which are useful in increasing gastric motility, in preventing emesis and emesis caused by anticancer treatments, anxiety, certain arrhythmias, and disorders caused by serotonin imbalances.

8 Claims, No Drawings

HETEROCYCLIC CARBOXYLIC ACID AMIDES AND ESTERS OF AZABICYCLIC COMPOUNDS AS GASTRIC PROKINETIC, ANTIEMETIC, ANXIOLYTIC AND ANTIARRHYTHMIC AGENTS

BACKGROUND OF THE INVENTION

1. Field of Invention

Novel 5-aminomethyl- and 5-hydroxymethyl-1-azabicyclo[3.2.1]octanes and 5-aminomethyl- and 5-hydroxymethyl-1-azabicyclo[3.3.1]nonanes are coupled with aryl carboxylic acids to obtain the corresponding amides and esters. These novel amides and esters, their optical isomers, and their pharmaceutically acceptable salts are useful in increasing gastric motility, in preventing emesis including emesis caused by cytotoxic agents and radiation treatment associated with cancer therapy, in treating anxiety, and in controlling or modulating disorders attributed to serotonin imbalance such as cognitive dysfunction, migraine, or psychosis.

2. Information Disclosure Statement

A number of patents pertain to arylcarboxylic amides and esters of azabicyclic ring systems formed from amino- and hydroxy-azabicicyloalkanes where the amino or hydroxy group is attached to a carbon other than a bridgehead carbon. For example, U.S. Pat. Nos. 4,593,034; 4,657,911 and 4,820,715 describe compounds having the formula below:

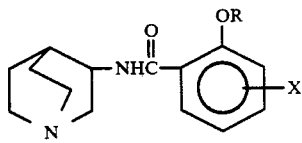

A German patent, German Offen. 2,748,260, describes azabicyclic amides of the formula:

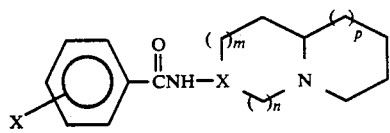

as having antiemetic and gastrokinetic utility. Class I antiarrhythmic compounds of the formula:

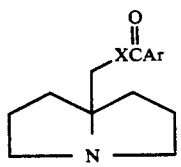

where X is O or NH are disclosed in EP207514A2 (CA106:1 56279r), JP 59/18417A2 (CA 102:45772a), JP 58/83694A2 (CA 99:122292m) and EP 39903A2 (CA 96:85419y). Unlike the compounds of the present invention these bridgehead substituted compounds have no intervening carbon between the bridgehead position and the ring nitrogen.

A European patent EP 094742A, and other subsequent patents, discloses compounds having the formula:

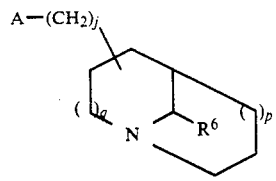

where $p=0-2$, $q=0-3$, $j=0-4$, A is ArCONH and the benzamide NH and the ring nitrogen are separated by at least 2 carbon atoms. This generic formula broadly encompasses the compounds of the present invention. However, there are no claims made to any compound where the A-$(CH_2)_j$- group is attached at the bridgehead position nor are there any examples or synthetic methods described which would support a bridgehead substitution. The intermediate azabicycloketones described preclude bridgehead substitution.

The arylcarboxylate amides and esters of the 5-aminomethyl- or 5-hydroxymethyl-1-azabicyclo[3.2.1]octanes or 1-azabicyclo[3.3.1]nonanes of this invention have not previously been described.

SUMMARY OF THE INVENTION

The present invention discloses compounds having the formula:

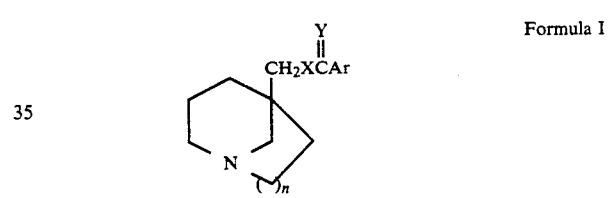

Formula I wherein n is 1 or 2
X is NH or O,
Y is O or S and
Ar is

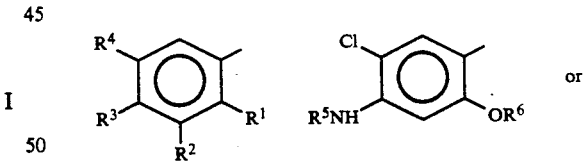

or

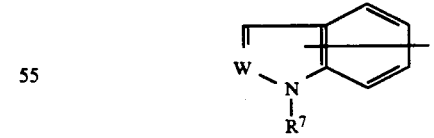

wherein
$R^1$, $R^2$, $R^3$ and $R^4$ are independently selected from the group consisting of H, halogen, $C_1$-$C_4$ alkyl, $C_1$-$C_4$ alkoxy, hydroxy, amino, $C_1$-$C_4$ alkylamino, $C_1$-$C_4$ dialkylamino, $C_2$-$C_4$ alkenyl, $CH_3SO_2NH$, or $SO_2NH_2$;
$R^5$ is H or $CH_3$,
$R^6$ is selected from the group consisting of H, $C_2$—$C_4$ alkenyl, —$CH_2CH_2SCH_3$,

W is CH or N, and
$R^7$ is H or $C_1$-$C_4$ alkyl, the stereoisomers;
the N-oxide;
or a pharmaceutically acceptable salt thereof.

In a further definition of the terms above, $C_1$-$C_4$ alkyl would include methyl, ethyl, propyl, isopropyl, butyl, isobutyl, and tertiarybutyl. The term $C_1$-$C_4$ alkoxy refers to the group -O-$C_1$-$C_4$ alkyl where $C_1$-$C_4$ alkyl is defined above. $C_2$-$C_4$ alkenyl includes ethenyl, propenyl, butenyl, or isobutenyl. Halogen means fluorine, chlorine, bromine, or iodine. Stereoisomers includes the geometric and optical isomers. These isomers can be obtained by standard methods for resolving optical isomers known to those skilled in the art. Pharmaceutically acceptable salts includes the acid addition salts, solvates, hydrates, and oxides of the tertiary nitrogen of the azabicyclic ring system. Acid addition salts are those salts formed from the basic Formula I compound and an inorganic acid such as hydrochloric acid, hydrobromic acid, sulfuric acid, or phosphoric acid or an organic acid such as fumaric acid, citric acid, maleic acid, hexamic acid, succinic acid and the like.

The stereoisomers can be separated using standard optical resolution techniques known to those skilled in the art. This invention also encompasses the novel intermediates used to prepare the Formula I compounds and the process for their preparation. These intermediates are represented by Formula 2 below wherein n is 1 or 2 and

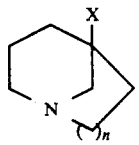

Formula 2

X is $CO_2R$, —CH=NOH, $CH_2NH_2$ or $CH_2OH$ where R is H, methyl or ethyl.

Objects of this invention are: (1) to provide novel arylcarboxylic acid amide and ester derivatives derived from the bridgehead functionalized 1-azabicyclo[3.2.1]octan-5-methanamine or methanol and 1-azabicyclo[3.3.1]nonan-5-methanamine or methanol, (2) to provide novel bridgehead functionalized azabicyclic intermediates, (3) to provide a method of treatment for impaired gastric motility, (4) to provide a method of treating emesis and emesis caused by anticancer radiation therapy and administration of anticancer drugs such as cisplatin, mechlorethamine hydrochloride, doxorubicin, dactinomycin and dacarbazine, (5) to provide a method of treating anxiety, (6) to provide a method of treating Class III arrhythmia, and (7) to provide a method of treating disorders of serotonin imbalances such as psychoses, migraine, and cognitive dysfunction by selective anatagonism of certain actions of serotonin.

Gastric motility enhancement is determined by measuring the amount of a test meal emptied from rats' stomachs in a given time period. Antiemetic properties are determined by measuring the reduction in emetic episodes included by administrator of the anticancer drug, cisplatin, in dogs. Anxiolytic activity is determined using the exploratory light/dark behavioral testing apparatus in mice. The ability of a test compound to block the hyperactivity induced by intracerebral administration of (+)amphetamine in rat nucleus accumbens is an indication of antipsychotic activity. Cognitive function activity is a measure of the ability of a compound to reverse the effect of scopolamine on learned behavior (location of food in T-maze). Selective serotonin antagonism is determined using the von Bezold-Jarisch reflex. Compounds which are active in this test are reported to be useful in alleviation of migraine, cluster headache, and trigeminal neuralgia, enhancing cognitive function and treating psychosis is warm-blooded animals.

DETAILED DESCRIPTION OF THE INVENTION

The novel compounds and their intermediates of this invention are prepared in a two-part process consisting of (A) the preparation of the intermediate 1-azabicyclo[3.2.1]octan-5-methananamine or methanol or 1-azabicyclo[3.3.1]nonan-5-methanamine or methanol and (B) coupling the amines or alcohols with carboxylic acid derivatives to obtain the amides and esters of this invention.

(A) The intermediates are prepared in several steps according to the following reaction schemes (i)--(iv):

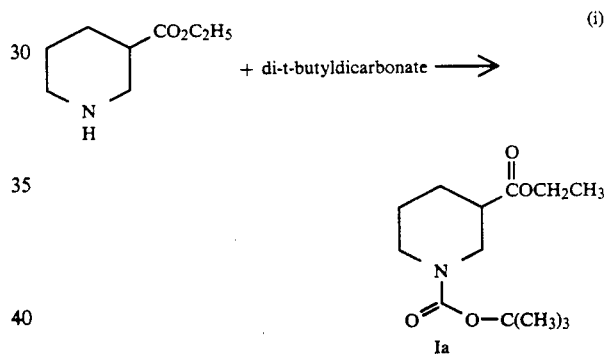

In scheme (i), nipecotic acid ethyl ester is reacted with di-t-butyldicarbonate to obtain the 1-tert-butyloxycarbonyl protected ester 1a.

Alternatively, nipecotic acid may be the starting material which is first converted to the methyl ester by reacting with thionyl chloride in methanol and then protecting the piperidine ring nitrogen using di-t-butyl dicarbonate (ii).

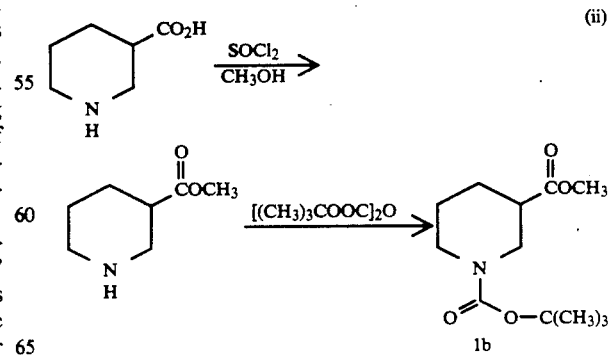

(iii) The t-BOC (t-butyloxycarbonyl) protected nipecotic acid ester (1a or 1b) is then treated with a strong base such as lithium diisopropylamide and the resulting carbanion reacted with a 1,2-dihaloethane or 1,3-dihalopropane. The alkylated intermediate undergoes a ring closure reaction when the t-BOC group is removed with trifluoroacetic acid giving the appropriate bridgehead carboxylic acid ester of the 1-azabicyclo[3.2.1]octane or 1-azabicyclo[3.3.1]nonane.

Method 2.

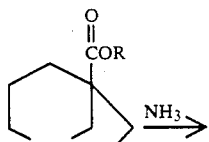

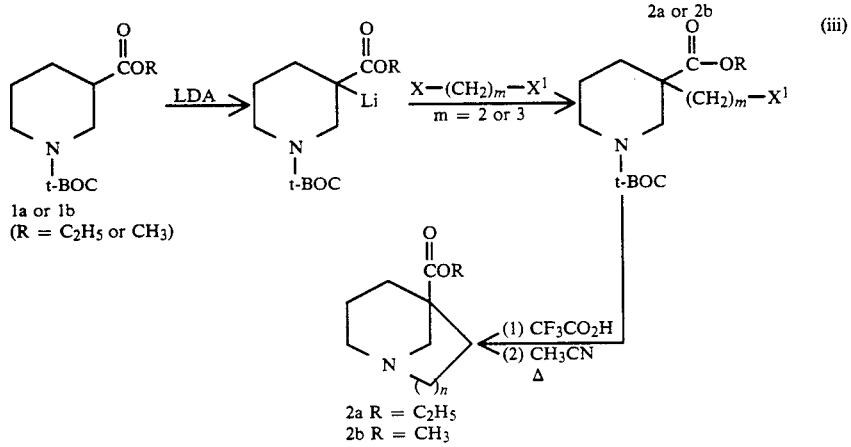

(iii)

(iv) Reduction of the ester 2a (or 2b) with a reducing agent capable of reducing an ester group such as lithium aluminum hydride (LAH) gives the 1-azabicyclo[3.2.1]octan-5-methanol or 1-azabicyclo[3.3.1]nonan-5-methanol depending on the value of n.

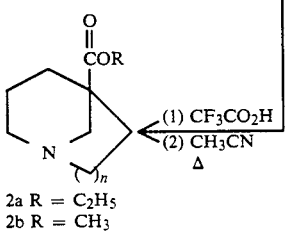

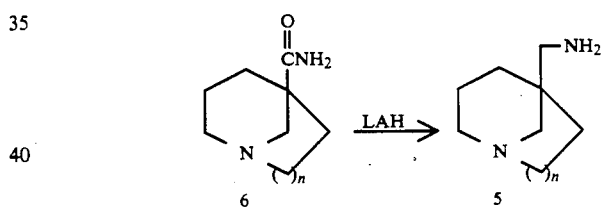

The aminomethyl intermediates 5 (1-azabicyclo[3.2.1]octan-5-methanamine or 1-azabicyclo[3.3.1]nonan-5-methanamine) are prepared according to methods 1 or 2.

B. The compounds of this invention are prepared by condensing an azabicyclic methanamine 5 or methanol 3 with an aryl carboxylic acid or heterocyclic carboxylic acid by the methods shown in the following reaction schemes (v)-(viii). The corresponding thioamides are prepared according to reaction scheme (ix).

Method 1.

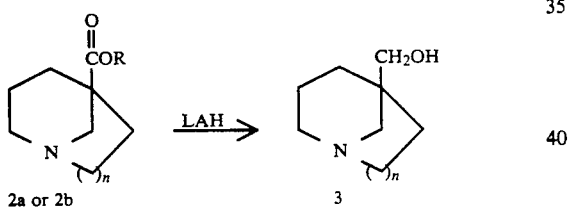

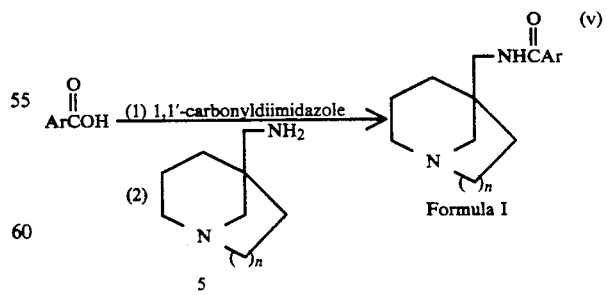

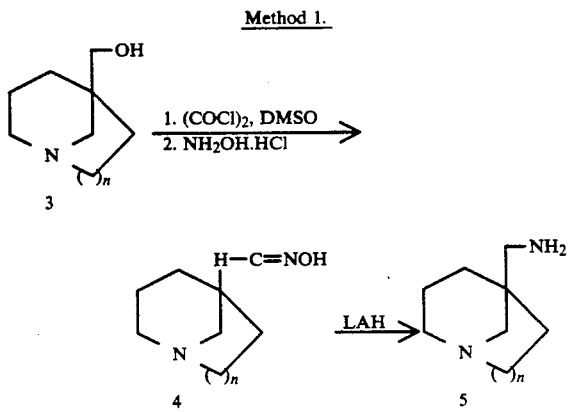

The intermediate carboxaldehyde is generated in situ and reacted with hydroxylamine hydrochloride to obtain the carboxaldehyde oxime (4).

The arylcarboxylic acid is reacted with 1,1'-carbonyldiimidazole in a dry aprotic solvent, such as tetrahydrofuran, forming in situ a 1-aroylimidazole which, when treated with an amine 5, forms the invention compound Formula I amide (X=NH).

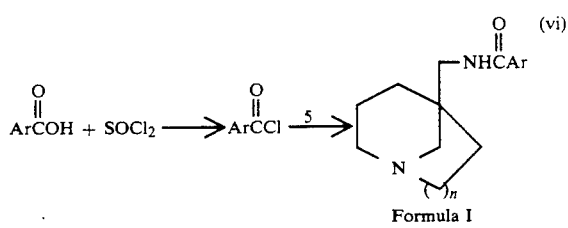

(vi)

The aryl carboxylic acid is reacted with thionyl chloride to form the corresponding acid chloride which is freed from thionyl chloride and reacted in an appropriate solvent or solvent mixture with an amine 5 to obtain a Formula I amide (X=N H).

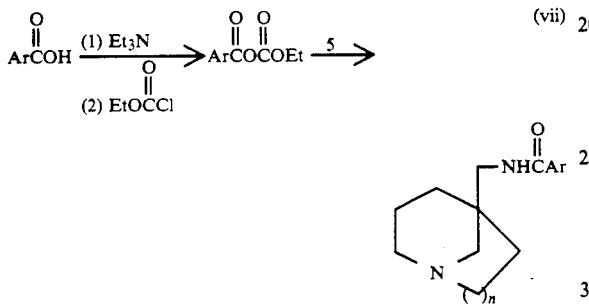

(vii)

By this procedure the arylcarboxylic acid is treated with an tertiary amine such as triethylamine in an aprotic solvent such as methylene chloride at or below ambient temperature to form a salt which is treated with a chloroformate, such as ethyl chloroformate, preferably at room temperature or below, forming a mixed acid anhydride. Without isolation the solution containing the mixed anhydride is treated with an amine 5 to give an amide of Formula I (X=NH).

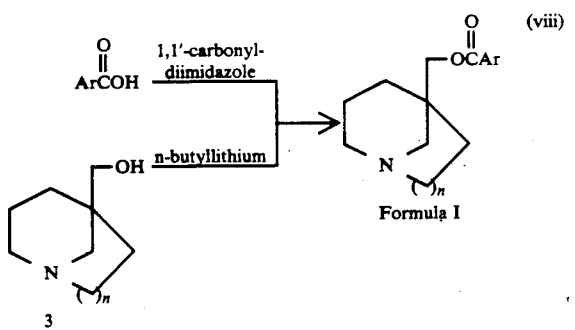

(viii)

Synthesis of Formula I esters is accomplished by a modification of reaction (v) whereby the 1-azabicyclic methanol 3 is reacted with a strong base such as n-butyllithium to form the alkoxide anion which reacts with the 1-aroylimidazole formed in situ to give the Formula I ester.

In some cases, it may be possible to isolate and purify the reaction intermediate 1-arolimidazole formed from the aryl carboxylic acid and 1,1'-carbonyldiimidazole.

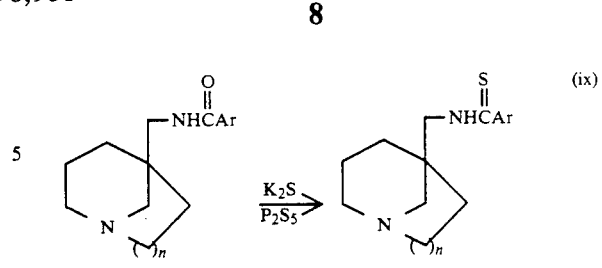

(ix)

The thioamides are prepared by reacting the amide with sulfurizing reagents such as potassium sulfide and phosphorus pentasulfide by known procedures.

The following Preparations and Examples are illustrative of the reaction schemes described broadly above and this disclosure should not be construed as limiting in any way. Other synthetic procedures for the preparation of intermediates and compounds of this invention will be apparent to those skilled in the art. It is believed that one skilled in the art will be able to carry out this invention without undue experimentation. The various reagents used in the following Preparations and Examples are either commercially available or readily synthesized by procedures given in the chemical and patent literature.

PREPARATION 1

1,3-Piperidinedicarboxylic acid 1-(1,1-dimethylethyl) 3-ethyl ester,

To a solution of nipecotic acid ethyl ester (44.0 g, 280 mmol) in methylene chloride (80 mL) was added dropwise to a solution of di-t-butyldicarbonate (61.2 g, 280 mmol) in methylene chloride (80 mL). The solution was stirred for 1 hour at room temperature, then filtered through Celite and concentrated in vacuo. The residue was distilled (bp$_{0.7}$ 124°–127° C.) to afford 67.5 g (94%) of the product as a colorless solid; mp 36°–38° C.

PREPARATION 2

1,3-Piperidinedicarboxylic acid 1-(1,1-dimethylethyl) 3-methyl ester

A cooled (−10° C.) solution of nipecotic acid (24.6 g, 190 mmol) in absolute methanol (200 mL) under a drying tube was treated dropwise with thionyl chloride (28 mL, 380 mmol) at a rate so as to keep the temperature −5° C., then the mixture was refluxed for 6 hours and concentrated in vacuo to a solid under a potassium hydroxide trap. The solid was dissolved in water (150 mL), and the aqueous solution was slowly basified with solid potassium carbonate (50 g), then further saturated with sodium chloride and extracted with methylene chloride (4×100 mL). The combined organic solution was dried (Na$_2$SO$_4$), concentrated in vacuo, redissolved in anhydrous methylene chloride (50 mL), and slowly added to a solution of di-t-butyldicarbonate (35.0 g, 160 mmol) in anhydrous methylene chloride (50 mL) the effervescent solution was stirred for one hour at room temperature, then filtered through Celite and concentrated in vacuo. The residual oil was distilled (bp 121°–124° C. at 0.8 mm) to afford 33.90 g (73%) of colorless solid; mp 47.5°–48.5° C.

Analysis: Calculated for C$_{12}$H$_{21}$NO$_4$: C, 59.24; H, 8.70; N, 5.76. Found: C, 59.27; H, 8.97; N, 5.75.

PREPARATION 3

1-Azabicyclo[3.2.1]octane-5-carboxylic acid ethyl ester

A cooled (−40° C.) solution of 1,3-piperidinedicarboxylic acid 1-(1,1-dimethylethyl) 3-ethyl ester (5.15 g, 20 mmol) in anhydrous tetrahydrofuran (25 mL) under nitrogen was treated (via syringe) with 1.15N lithium diisopropylamide/tetrahydrofuran (21 mmol, 18.3 mL), stirred for one hour at −15±5° C., cooled (−40° C.), and treated with 1-bromo-2-chloroethane (3.6 g, 25 mmol). The solution was warmed to room temperature over one hour, stirred at 40° C. for 15 minutes, and most of the solvent was removed in vacuo and replaced with methylene chloride (100 mL). The organic solution was washed with saturated aqueous sodium bicarbonate (50 mL), and the aqueous extract was backwashed with methylene chloride. The combined organic solution was washed with brine (50 mL), dried ($Na_2SO_4$), concentrated in vacuo, and filtered through a short column of alumina (eluted with methylene chloride). The concentrated filtrate was taken up in anhydrous methylene chloride (10 mL), cooled (0° C.), and treated dropwise with trifluoroacetic acid solution (6 mL). After one hour at room temperature and 15 minutes at 40° C., the solution was concentration in vacuo and partitioned between methylene chloride (100 mL) and saturated aqueous sodium carbonate (60 mL). The organic layer was separated and the aqueous solution was extracted with methylene chloride (2×50 mL). The combined organic solution was dried ($Na_2SO_4$), concentrated in vacuo, dissolved in acetonitrile (100 mL), and refluxed for 2 hr. Most of the acetonitrile was removed in vacuo and replaced with methylene chloride (100 mL), and the above detailed extraction procedure with saturated aqueous sodium carbonate (60 ml) was repeated. The crude residue was subjected to bulb-to-bulb distillation (bp 90°–100° C. at 0.7 mm Hg) to afford 2.51 g (68%) of colorless non-viscous oil.

For analysis, a portion of the oil (0.18 g, 1.0 mmol) in anhydrous tetrahydrofuran (5 mL) was treated with excess HBr/methylene chloride solution, and the solution was concentrated in vacuo. The residue was triturated from ether and dried exhaustively in vacuo (1.0 mm pressure) at 80° C. to afford 0.23 g (87%) of the hydrobromide and of the title compound as a slightly hygroscopic pale yellow solid; mp 95.5–97.5° C.

Analysis: Calculated for $C_{10}H_{17}NO_2 \cdot HBr$: C, 45.75; H, 6.87; N, 5.30. Found: C, 45.16; H, 6.99; N, 5.30.

PREPARATION 4

1-Azabicyclo[3.3.1]nonane-5-carboxylic acid ethyl ester

A cooled (−50° C.) solution of 1,3-piperidinedicarboxylic acid 1-(1,1-dimethylethyl) 3-ethyl ester (12.9 g, 50 mmol) in anhydrous tetrahydrofuran (60 mL) was treated (via syringe) with 1.15 N lithium diisopropylamide/tetrahydrofuran (52 mmol), stirred for one hour at −15±5° C., cooled (−35° C.), treated with 1-bromo-3-chloropropane (10.2 g, 65 mmol), warmed to room temperature over one hour, and stirred for 30 minutes. Most of the solvent was removed in vacuo, replaced with ether, and the organic solution was washed with saturated sodium bicarbonate (150 mL). The aqueous solution was extracted with ether (2×50 mL), and the combined organic solution was dried ($MgSO_4$), concentrated in vacuo, and passed through a short column of alumina (eluted with methylene chloride). The concentrated filtrate was dissolved in anhydrous methylene chloride (25 mL), cooled (10° C.), and treated dropwise with trifluoroacetic acid (15 mL). The solution was stirred for one hour at room temperature, 15 l minutes at 45° C., and concentrated in vacuo. The residue was partitioned between 1.25 N sodium carbonate (75 mL) and methylene chloride (100 mL), and the organic layer was separated. The aqueous solution was extracted with methylene chloride (2×50 mL), a the combined organic solution was dried ($Na_2SO_4$), concentrated in vacuo taken up in warm hexane, treated with a little charcoal, and filtered. The filtrate was concentrated in vacuo and the residue was distilled ($bp_{0.6}$ 83°–85° C.) to give 7.2 g (73%) of the product.

PREPARATION 5

1-Azabicyclo[3.3.1]nonane-5-carboxylic acid methyl ester

A cooled (−50° C.) solution of 1,3-piperidinedicarboxylic acid 1-(1,1-dimethylethyl) 3-methyl ester (12.9 g, 50 mmol) in anhydrous tetrahydrofuran (60 mL) was treated (via syringe) with 1.15 N lithium diisopropylamide/tetrahydrofuran (52 mmol), stirred for one hour at −15±5° C., cooled (−35° C.), treated with 1-bromo-3-chloropropane (10.2 g., 65 mmol), warmed to room temperature over one hour, and stirred for 30 minutes. Most of the solvent was removed in vacuo, replaced with ether, and the organic solution was washed with saturated sodium bicarbonate (150 mL). The aqueous solution was extracted with ether (2×50 mL), and the combined organic solution was dried ($MgSO_4$), concentrated in vacuo, and passed through a short column of alumina (eluted with methylene chloride). The concentrated filtrate was dissolved in anhydrous methylene chloride (25 mL), cooled (10° C.), and treated dropwise with trifluoroacetic acid (15 mL). The solution was stirred for one hour at room temperature, 15 minutes at 45° C., and concentrated in vacuo. The residue was partitioned between 1.25 N sodium carbonate (75 mL) and methylene chloride (100 mL), and the organic layer was separated. The aqueous solution was extracted with methylene chloride (2×50 mL), and the combined organic solution was dried ($Na_2SO_4$), concentrated in vacuo, and taken up in toluene (150 mL). The solution was refluxed for 8 hours, cooled to room temperature, and stirred for 15 minutes with 1.25 N sodium carbonate (75 mL). The organic layer was separated and the aqueous solution was extracted with ether (2×50 mL). The combined organic solution was dried ($MgSO_4$), concentrated in vacuo, taken up in warm hexane, treated with a little charcoal, and filtered. The filtrate was concentrated in vacuo to afford 3.63 g (37%) of colorless needles; mp 60°–62° C. (cold hexane).

Analysis: Calculated for $C_{10}H_{17}NO_2$: C, 65.54; H, 9.35; N, 7.64. Found: C, 65.54; H, 9.53; N, 7.65.

PREPARATION 6

1-Azabicyclo[3.2.1]octane-5-methanol

A cooled (0° C.) solution of 1.0 N lithium aluminum hydride/tetrahydrofuran (55 mL, 55 mmol) under nitrogen was treated dropwise with a solution of 1-azabicyclo[3.2.1]octane-5-carboxylic acid ethyl ester (9.17 g, 50 mmol) in anhydrous tetrahydrofuran (20 mL), stirred for 30 minutes at room temperature, refluxed for one hour, and cooled (0° C.). In sequence, water (2.1 mL), 15% sodium hydroxide solution (2.1 mL) and water (6.3 mL) were carefully added dropwise, and the mixture was filtered through Celite (the solid was washed with tetrahydrofuran) and concentrated in vacuo to afford 6.50 g (92%) of viscous, colorless oil, which can be used as is or can be solidified on cooling; mp 44°-47° C.

PREPARATION 7

1-Azabicyclo[3.2.1]octane-5-carboxaldehyde, oxime

A cooled (−65° C.) solution of oxalyl chloride (8.0 mL, 90 mmol) in anhydrous methylene chloride (150 mL) under nitrogen was treated dropwise with anhydrous dimethylsulfoxide (14.4 g, 180 mmol) in methylene chloride (45 mL) at a rate to keep the temperature below −60° C. After 30 minutes at −65±2° C., a solution of 1-azabicycl[3.2.1]octane-5-methanol (8.48 g, 60 mmol) in methylene chloride (45 mL) was added dropwise at a rate to keep the temperature below −55° C., and the mixture was stirred at −55±5° C. for one hour. Triethylamine (60 mL) was added (temperature below −50° C.), then the mixture was allowed to warm to room temperature over one hour and diluted with methylene chloride (200 mL). The organic solution was washed with water (200 mL), saturated sodium carbonate (200 mL), and brine (200 mL), with each extract backwashed, and the combined organic solution was dried ($Na_2SO_4$), concentrated in vacuo, and taken up in methanol (150 mL). Hydroxylamine hydrochloride (5.25 g, 75 mmol) was added, followed by 25% sodium methoxide/methanol (2.2 g), then the mixture was stirred 45 minutes at room temperature, 45 minutes at 50° C., cooled on an ice bath, and treated with additional 25% sodium methoxide (14.0 g). After five minutes the solution was filtered and the filtrate was concentrated in vacuo to a residue, which was filtered through a short column of aluminum (eluted with 2:1 tetrahydrofuran/methanol). This afforded, after concentration in vacuo, 4.40 g (48%) of pale yellow viscous oil, usable without further purification.

PREPARATION 8

1-Azabicyclo[3.2.1]octane-5-methanamine dihydrobromide

A cooled (0° C.) solution of 1-azabicyclo[3.2.1]octane-5-carboxaldehyde oxime (4.40 g, 28.5 mmol) in anhydrous tetrahydrofuran (20 mL) under nitrogen was treated dropwise with 1.0 N lithium aluminum hydride (60 mL, 60 mmol), stirred at room temperature for 30 minutes and at reflux for 2 hours, and cooled (0° C.). Water (2.3 mL), 15% sodium hydroxide (2.3 mL), and water (7.0 mL) were carefully added dropwise sequentially, and the suspension was filtered through Celite (washed with tetrahydrofuran). The filtrate was concentrated in vacuo and subjected to bulb-to-bulb distillation (bp 85°-95° C. at 0.7 mm pressure) to afford 2.35 g (59%) of colorless oil, which readily forms a carbonate.

A portion of the oil (0.14 g, 1.0 mmol) in anhydrous tetrahydrofuran (10 mL) was treated with excess HBr/methylene chloride solution and the suspension was filtered under nitrogen. The solid was collected and exhaustively dried at 110° C. and 1.0 mm pressure in the pressure of $P_2O_5$ and solid potassium hydroxide to afford 0.26 g (86%) of slightly hydroscopic, colorless solid; mp 265° C. (dec).

Analysis: Calculated for $C_9H_{16}N_2 \cdot 2HBr$: C, 31.81; H, 6.01; N, 9.27. Found: C, 31.58; H, 6.40; N, 9.50.

PREPARATION 9

1-Azabicyclo[3.3.1]nonane-5-methanol,

A solution of 1-azabicyclo[3.3.1]nonane-5-carboxylic acid ethyl ester (9.08 g, 46 mmol) in anhydrous tetrahydrofuran (25 mL) was added dropwise to a cooled (−10° C.) solution of 1.0N lithium aluminum hydride/tetrahydrofuran (50 mL, 50 mmol) in a 3-neck, 250-mL flask under nitrogen at a rate to keep the reaction temperature below 1 5° C., The mixture was stirred for 15 minutes at room temperature, refluxed for 45 minutes, cooled (0° C.), and carefully treated dropwise with water (2 mL), 15% sodium hydroxide (2 mL), and water (6 mL). The suspension was filtered through Celite and the solid was washed with tetrahydrofuran. The filtrate was concentrated in vacuo to afford 6.99 g (98%) of colorless solid; mp 64.0°-65.5° C.

Analysis: Calculated for $C_9H_{17}NO$: C, 69,63; H, 11.04; N, 9.02. Found: C, 69.53; H, 11.18; N, 8.95.

PREPARATION 10

1-Azabicyclo[3.3.1]nonane-5-carboxaldehyde oxime

A cooled (−65° C.) solution of oxalyl chloride (5.3 mL, 60 mmol)in anhydrous methylene chloride (100 mL) under nitrogen was treated dropwise with anhydrous dimethylsulfoxide (0.60 g, 120 mmol) in methylene chloride (30 mL) at a rate to keep the reaction temperature below −60° C. After 30 minutes at −65° C., a solution of 1-azabicyclo[ 3.3.1]nonane-5-methanol (6.21 g, 40 mmol) in methylene chloride (30 mL) was added dropwise at a rate to keep the reaction temperature below −55° C., and the mixture was stirred at −55±5° C. for one hour. Triethylamine (40 mL) was added the temperature was kept below −50° C.), then the mixture was allowed to warm to room temperature over one hour and diluted with methylene chloride (200 mL). The organic solution was washed with water (200 mL), saturated aqueous sodium carbonate (200 mL), and brine (200 mL), and each aqueous extract was backwashed with methylene chloride. The combined organic solution was dried ($Na_2SO_4$), concentrated in vacuo, and taken up in methanol (100 mL), then treated with hydroxylamine hydrochloride (3.5 g, 50 mmol) and 25% sodium methoxide/methanol (1.8 g). After 2 hours at room temperature, additional 25% sodium methoxide (9.0 g) was added, and the mixture was warmed to 45° C. for 30 minutes, then partially concentrated and diluted with methylene chloride (150 mL). The organic solution was washed with saturated aqueous sodium carbonate (100 mL), and the aqueous layer was salted with potassium carbonate and extracted with methylene chloride (3×100 mL). The combined organic solution was dried ($Na_2SO_4$), concentrated in vacuo, and recrystallized from acetonitrile (2 crops) to afford 4.03 g (60%) of colorless crystals; mp 115°-117° C.

Analysis: Calculated for $C_9H_{16}N_2O$; C, 64.25; H, 9.59; N, 16.65. Found: C, 64.26; H, 9.73; N, 16.67.

PREPARATION 11

1-Azabicyclo[3.3.1]nonane-5-methanamine dihydrochloride

A cooled (0° C.) solution/suspension of 1-azabicyclo[3.3.1]nonane-5-carboxaldehyde oxime (0.34 g, 2 mmol) in anhydrous tetrahydrofuran (2 mL) was carefully treated dropwise (via syringe) with 1.0N lithium aluminum hydride/tetrahydrofuran (4.0 mL, 4 mmol), then refluxed for one hour and cooled (0° C.). The mixture was carefully treated dropwise with water (0.15 mL), 15% sodium hydroxide (0.15 mL),and water (0.5 mL), and the mixture filtered through Celite (washed with tetrahydrofuran). This solution was treated with excess ethereal HCl, the suspension was filtered, and the solid was triturated form warm acetonitrile and vacuum dried (1.0 mmHg at 110° C.) in the presence of KOH and phosphorous pentoxide to afford 0.32 g (70%) of colorless solid; mp 310° (dec).

Analysis: Calculated for $C_9H_{19}N_2.2HCl$: C, 47.58; H, 8.87; N, 12.33. Found: C, 47.34; H, 9.09; N, 12.25.

PREPARATION 12

1-Azabicyclo[3.3.1]nonane-5-carboxamide

A solution of 1-azabicyclo[3.3.1]nonane-5-carboxylic acid methyl ester (1.83 g, 10 mmol) in ammonia (50 mL) and methanol (20 mL) was sealed in a bomb and heated at 120°–130° C. for 36 hours (gas chromatography indicated that the reaction was incomplete). Three drops of 25% sodium methoxide/methanol were added, and the mixture was heated at 130° C. for 21 hours and at 150° C. for 72 hours, at which time the reaction was essentially complete. The solution was concentrated in vacuo and the residue was partitioned between 1.25 N sodium carbonate (50 mL) and methylene chloride (75 mL). The organic layer was separated and the aqueous solution was extracted with methylene chloride (2×40 mL). The combined organic layers were dried ($Na_2SO_4$), concentrated in vacuo, and recrystallized from acetonitrile to afford 0.64 g (38%) of pale brown solid: mp 172.5°–175.0° C.

Analysis: Calculated for $C_9H_{16}N_2O$: C, 64.25; H, 9.59; N, 16.65. Found: C, 64.04; H, 9.68; N, 16.70.

PREPARATION 13

1-Azabicyclo[3.3.1]nonane-5-methanamine,

A suspension of 1-azabicyclo[3.3.1]nonane-5-carboxamide (1.80 g, 10.7 mmol) in anhydrous tetrahydrofuran (10 mL) under nitrogen was treated (via syringe) with 1.0 N lithium aluminum hydride/tetrahydrofuran (25 mL, 25 mmol),and the mixture was refluxed for 4 hours and cooled (0° C.). The mixture was treated carefully dropwise sequentially with water (1 mL), 15% sodium hydroxide (1 mL), and water (3 mL). Ether (50 mL) was added, the mixture was filtered through Celite, and the filter cake was washed with ether. The filtrate was concentrated in vacuo to afford 1.27 g (77%) of colorless oil.

PREPARATION 14

1-Azabicyclo[3.2.1]octane-5-methanol monohydrobromide

A cooled (0° C.) solution of 1.0 N lithium aluminum hydride/tetrahydrofuran (55 mL, 55 mmol) under nitrogen was treated dropwise with a solution of 1-azabicyclo[3.3.1]nonane-5-carboxylic acid ethyl ester (9.17 g, 50 mmol) in anhydrous tetrahydrofuran (20 mL), stirred for 30 minutes at room temperature, refluxed for one hour, and cooled (0° C.). Water (2.1 mL), 15% sodium hydroxide (2.1 mL), and water (6.3 mL) were carefully added dropwise sequentially, and the mixture was filtered through Celite (the solid was washed with tetrahydrofuran) and concentrated in vacuo to afford 6.50 g (92%) of viscous, colorless oil, which can be used as is or can be solidified on cooling; mp 45°–47° C.

A portion of the oil (0.28 g, 2 mmol) in anhydrous tetrahydrofuran (2 mL) was treated with excess HBr/methylene chloride, stirred for 5 minutes, and filtered (solid was washed with tetrahydrofuran). The solid was triturated from cold acetonitrile to afford (after drying) 0.40 g (90%) of a colorless solid; mp 250° C.(dec).

Analysis: Calculated for $C_9H_{15}NO.HBr$; C, 43.26; H, 7.26; N, 6.31. Found: C, 43.06; H, 7.52; N, 6.29.

PREPARATION 15

1-Methyl-1H-indole-3-carboxylic acid

A cooled (0° C.) suspension of 60% sodium hydride-oil dispersion (0.96 g, 24 mmol) in anhydrous N,N-dimethylformamide (15 mL) under nitrogen was treated in portions with in dole-3-carboxylic acid (1.62 g, 10 mmol), and the mixture was stirred at 45±5° C. for 30 minutes. Dimethylsulfate (3.03 g, 24 mmol) was added, and the mixture was heated to 100° C. for 30 minutes, cooled, and added to ice water (100 mL). The suspension was filtered and the wet solid was washed with water and taken up in 50% aqueous methanol (40 mL). The mixture was treated with 50% aqueous sodium hydroxide (3.0 g, 37.5 mmol) and refluxed for 30 minutes, then them ethanol was removed in vacuo and replaced with water. The aqueous solution was extracted with ether (50 mL), the acidified with 3N HCl to pH 3 (15 mL). The suspension was filtered and the solid was washed with water and dried exhaustively m vacuo in the presence of Drierite. Recrystallization from acetonitrile afforded 1.32 g (75%) of colorless crystals; mp 201°–202° C. (dec).

Analysis: Calculated for $C_{10}H_9NO_2$: C, 68.56; H, 5.18; N, 8.00. Found: C, 68.42; H, 5.05; N, 7.97.

PREPARATION 16

1-Methyl-1H-indazole-3-carboxylic acid

A solution of 1-methylindazole-3-carboxylic acid, methyl ester (1.00 g, 0.0053 mol) was stirred in a mixture of methanol (10 mL)/2 N NaOH solution (120 mL) at reflux temperature for 2 hours. After cooling, the mixture was diluted with water (100 mL) and acidified with 6 N HCl solution. The white solid that formed was collected by filtration and dried under ambient conditions for 6 days to give 0.86 g (92% yield) of the product; mp 215°–216° C.

Analysis: Calculated for $C_9H_9N_2O_2$: C, 61.36; H, 4.58; N, 15.90. Found: C, 61.25; H, 4.53; N, 15.89.

PREPARATION 17

4-Amino-5-chloro-2-hydroxybenzoic acid,

A cooled (5° C.) suspension of 60% sodium hydride/oil dispersion (20.0 g, 0.50 mole) in anhydrous dimethylformamide (300 mL) under nitrogen was treated slowly dropwise with ethyl mercaptan (18.7 g, 0.30 mole) so as to maintain a pot temperature below 15° C., then stirred at room temperature for 15 minutes, cooled (5° C.), and treated in portions with 4-amino-5-chloro-2-methoxybenzoic acid (40.33 g, 0.20 mole). The mixture was heated to 105±5° C. for 4 hours, cooled, and concentrated in vacuo to remove most of the dimethylformamide, then plunged into water (500 mL). The aqueous solution was extracted with methylene chloride (2×150 mL), and ether (150 mL), acidified with concentrated HCl (55 mL), filtered, and the filter cake washed with water and dried in vacuo to afford 35.7 g of crude product. Crystallization from tetrahydrofuran/hexane afforded 31.3 g (83%) of white solid; mp 192° C.

PREPARATION 18

4-Amino-5-chloro-2-hydroxybenzoic acid, methyl ester

A solution of 4-amino-5-chloro-2-hydroxybenzoic acid (1.88 g, 10 mmol) in absolute methanol (20 mL) was treated with 25% sodium methoxide/methanol (2.16 g, 10 mmol), stirred for 30 minutes, and concentrated in vacuo. The solid residue was taken up in anhydrous acetone (30 mL), treated with dimethyl sulfate (1.64 g, 13 mmol), and refluxed for 2 hours. The resultant solution was diluted with water (100 mL), and the precipitate was filtered, washed with water, and dried exhaustively in vacuo to afford 1.75 g (87%) of fine colorless needles. The material was recrystallized from ethyl acetate/hexane; mp 138°-139° C.

Analysis: Calculated for $C_9H_9ClNO_3$: C, 47.66; H, 4.00; N, 6.95. Found: C, 47.60; H, 4.00; N, 6.93.

PREPARATION 19

4-Amino-5-chloro-2-(2-methoxyethoxy)benzoic acid methyl ester,

A suspension of 60% sodium hydride/oil dispersion (1.00 g, 25 mmol) in anhydrous dimethylformamide (40 ml) under nitrogen was treated with 4-amino-5-chloro-2-hydroxybenzoic acid methyl ester (4.03 g, 20 mmol), stirred for 30 minutes, then treated with 2-bromoethyl methyl ether (3.48 g, 25 mmol). The mixture was heated to 95±5° C. for 1.5 hours, then cooled and added to water (250 mL). The aqueous suspension was filtered, and the solid was washed with water, air dried, collected, and recrystallized from ether/hexane to afford 2.75 g (53%) of the tile compound; mp 121.0°-122.5° C.

PREPARATION 20

4-Amino-5-chloro-2-(2-methoxyethoxy)benzoic acid

A solution of 4-amino-5-chloro-2-(2-methoxyethoxy)-benzoic acid methyl ester (2.75 g, 10.6 mmol) in 95% ethanol (20 mL) was treated with 50% sodium hydroxide (10 mL) and water (10 mL), and refluxed for one hour. The ethanol was removed in vacuo and replaced with water. The aqueous solution was extracted with ether (20 mL) and acidified to pH 4 with concentrated hydrochloric acid (16 mL). A solid soon precipitated, and this was filtered, washed with water, air dried, and recrystallized from ethyl acetate (2 crops) to afford 2.03 g (75%) of fine pale tan needles; mp 119°-120° C.

Analysis: Calculated for $C_{10}H_{12}ClNO_4$: C, 48.89; H, 4.92; N, 5.70. Found; C, 48.87; H, 4.94; N, 5.68.

PREPARATION 21

4-[(Methylsulfonyl)amino]benzoic acid methyl ester

A solution of methanesulfonyl chloride (15.2 g, 132 mmol) in methylene chloride (50 mL) was added dropwise to a stirring slurry of pyridine (41.8 g, 529 mmol) and methyl-4-aminobenzoate (20.0 g, 132 mmol) in methylene chloride (110 mL) cooled by a dry ice/acetone bath. The reaction mixture was allowed to warm to ambient temperature and was stirred overnight. The reaction mixture was added to 400 mL of 4% aqueous HCl solution and the solid that formed was collected by filtration. The orange solid was recrystallized from methanol to give 28.8 g (91.5%) of an orange-pink solid, mp 147°-150° C.

Analysis; Calculated For $C_9H_{11}NO_4S$; C, 47.15; H, 4.84; N, 6.11. Found: C, 47.12; H, 4.86; N, 6.11.

PREPARATION 22

4-[(Methylsulfonyl)amino]benzoic acid

4-[(Methylsulfonyl)amino]benzoic acid methyl ester (33.1 g, 145 mmol) was added to a 3:1 mixture of tetrahydrofuran and water (450 mL). To this slurry was added 1.2 equivalents of lithium hydroxide hydrate (7.29 g, 174 mmol). After a solution formed (about 15 min) an additional 1.1 equivalent of lithium hydroxide hydrate (6.68 g, 159 mmol) was added, and the reaction was stirred overnight. The 2 layers which formed were separated, and the aqueous layer was washed with ether (100 mL) and concentrated. The residue was azetroped with ethanol (2×200 mL) to give a white solid (dilithium salt). the white solid was suspended in 200 mL of ethanol and the slurry was made acidic with concentrated hydrochloric acid. The slurry was warmed until a solution formed. Upon cooling a solid formed which was collected by filtration. The solid was recrystallized from methanol to give 17.5 g (78%) of white solid, mp 240°-243° C.

Analysis: Calculated for $C_9H_9NO_4S$: C, 44.64; H, 4.22; N, 6.51. Found: C, 44.50; H, 4.21; N, 6.47.

PREPARATION 23

4-Amino-5-chloro-2-[2-(diethylamino)-2-oxyethoxyl-benzoic acid, methyl ester,

A cooled (0° C.) suspension of 60% sodium hydride/oil dispersion (1.40 g, 35 mmol) in anhydrous dimethylformamide (60 mL) under nitrogen was treated in portions with 4-amino-5-chloro-2-hydroxybenzoic acid methyl ester (6.05 g, 30 mmol) and stirred for 30 minutes at room temperature. 2-Chloro-N,N-diethylacetamide (5.40 g, 36 mmol) was added, and the mixture was stirred at 100°-110° for 3 hours until gas chromatography indicated absence of the ester starting material. The solution was cooled and added to ice water (350 mL), then extracted with ether (3×200 mL). The combined organic solution was dried (MgSO4) and concentrated in vacuo. Filtration through alumina (eluted with 3% methanol/methylene chloride) and trituration from petroleum ethers (30°-60° ) afforded 8.66 g (92%) of the product as a colorless solid; mp 97.5°-99.5° C. (ethyl acetate/hexane).

PREPARATION 24

4-Amino-5-chloro-2-[2-(diethylamino)-2-oxoethoxyl-benzoic acid,

A solution of 4-amino-5-chloro-2-[2-(diethylamino)-2-oxoethyoxy]benzoic acid, methyl ester (7.87 g, 25 mmol) in water (70 g) containing methanol (40 g) was treated with 50% sodium hydroxide (10 g) and heated to 60° C. for 30 minutes. The mixture was neutralized with 3N HCl until a precipitate formed (pH 3),and the solid was collected, washed with water, air dried, and recrystallized from 2-propanol to afford (2 crops) 5.12 g (68%) of fine colorless needles; mp 186.5°-188.0° C.

Analysis: Calculated for $C_{13}H_{17}ClN_2O_4$: C, 51.92; H, 5.70; N, 9.31. Found: C, 52.02; H, 5.78; N, 9.32.

PREPARATION 25

3-(1H-Imidazol-1-ylcarbonyl)-1-methyl-1H-indazole,

A suspension of 1-methyl-1H-indazole-3-carboxylic acid (2.65 g, 15 mmol) in anhydrous tetrahydrofuran (20 mL) under nitrogen was treated with 1,1-carbonyldiimidazole (2.76 g, 17 mmol). The mixture was gently warmed until bubbling and dissolution began, after a few minutes all solid dissolved and a new precipitate began to form. Stirring was continued for one hour, then anhydrous ether (20 mL) was added and the suspension was cooled (0° C.), filtered, and the solid washed with ether. Drying in vacuo at 50° C. afforded 3.01 g (89%) of colorless needles; mp (acetonitrile) 144.0°-145.5° C.

Analysis: Calculated for $C_{12}H_{10}N_4O$: C, 63.71; H, 4.46; N, 24.76. Found: C, 63.61; H, 4.33; N, 24.83.

PREPARATION 26

4-Amino-5-chloro-2-(2-propenyloxy)benzoic acid

A suspension of 60% sodium hydride/oil dispersion (1.52 g, 38 mmol) in anhydrous dimethylformamide (50 mL) under nitrogen was treated in portions with 4-amino-5-chloro-2-hydroxybenzoic acid methyl ester (6.05 g, 30 mmol), stirred at room temperature for 30 minutes, and treated with allyl bromide (4.60 ,g 38 mmol). The mixture was stirred at 95±5° C. for one hour, cooled to room temperature, and added to water (250 mL). The solid was removed by filtration and saved, and the filtrate was extracted with ether (2×100 mL). The concentrated ethereal extracts were combined with the filtrated solid, taken up in 20% aqueous ethanol (100 mL), treated with potassium hydroxide (10 g), and refluxed for 45 minutes. The ethanol was removed in vacuo and the aqueous solution was extracted with ether (50 mL) and petroleum ethers (30°-60°, 50 mL), cooled (0° C.), and acidified to pH 4 with concentrated hydrochloric acid (17 mL).

The suspension was filtered and the solid was air dried, dissolved in methylene chloride (150 mL) containing a line methanol, dried ($Na_2SO_4$), and concentrated in vacuo. Trituration from cold ether/petroleum ethers (30°-60°) and recrystallization from ethyl acetate/hexane (2 crops) afforded 4.25 g (62.2%) of a pale tan solid; mp 136°-137° C.

Analysis: Calculated for $C_{10}H_{10}ClNO_3$: C, 52.76; H, 4.43; N, 6.15. Found: C, 52.71; H, 4.42; N, 6.15.

PREPARATION 27

4-Amino-5-chloro-2-[2-(methylthio)ethoxylbenzoic acid

A cooled (5° C.) suspension of 60% sodium hydroxide oil dispersion (0.52 g, 13 mmoles) in anhydrous dimethylformamide (15 mL) under nitrogen was treated in portions with 4-amino-5-chloro-2-hydroxybenzoic acid (0.94 g, 5 mmoles), stirred for 15 minutes at 25° C., treated with (2-chloroethyl)methyl sulfide (1.66 g, 15 mmoles), and heated to 100° C. for 18 hours. The solution is cooled, concentrated in vacuo, and added to water (25 mL). The aqueous solution is extracted with ether, and the extract is dried ($MgSO_4$), concentrated in vacuo, taken up in 50% aqueous ethanol (50 mL), treated with potassium hydroxide (5.0 g), and refluxed for one hour. The mixture is concentrated, diluted with water to 75 mL total volume, extracted with ether, and acidified to pH 3 with concentration HCl. The precipitate is filtered, washed with water, air dried, and recrystallized from ethyl acetate to afford 0.74 g (57%) of product as fine voluminous white needles, mp 137.5°-139.5° C.

Analysis: Calculated for $C_{10}H_{12}ClNO_3S$: C, 45.89; H, 4.62; N, 5.35. Found: C, 45.96; H, 4.72; N, 5.32.

EXAMPLE 1

4-Amino-N-(1-azabicyclo[3.2.1]oct-5-ylmethyl)-5-chloro-2-methoxybenzamide

A suspension of 4-amino-5-chloro-2-methoxybenzoic acid (1.72 g, 8.5 mmol) in anhydrous tetrahydrofuran (10 mL) under nitrogen was treated with 1,1-carbonyldiimidazole (1.46 g, 9.0 mmol), stirred for one hour, then degassed under a stream of nitrogen for 10 minutes. A solution of 1-azabicyclo[3.2.1]octane-5-methanamine (1.27 g, 9.0 mmol) in anhydrous tetrahydrofuran (8 mL) was added, and stirring was continued at room temperature for 18 hours and at 50° C. for one hour. The mixture was concentrated in vacuo and partitioned between toluene (100 mL) containing a little 2-propanol and saturated sodium carbonate (50 mL). The organic layer was separated and the organic solution was dried ($Na_2SO_4$), concentrated in vacuo, and triturated from cold ether. Recrystallization from acetonitrile (2 crops) afforded 1.92 g (70%) of colorless crystals; mp 185°-187° C.

Analysis: Calculated for $C_{16}H_{22}ClN_3O_2$: C, 59.35; H, 6.85; N, 12.98. Found: C, 59.05; H, 6.98; N, 12.57.

EXAMPLE 2

N-(1-Azabicyclo[3.2.1]oct-5-ylmethyl)-5-chloro-2-methoxy-4-(methylaminobenzamide A solution of 5-chloro-2-methoxy-4-(methylamino)-benzoic acid (1.23 g, 5.7 mmol) in anhydrous tetrahydrofuran (6 mL) under nitrogen was treated with 1,1-carbonyldiimidazole (0.97 g, 6.0 mmol), stirred for one hour, then degassed under a stream of nitrogen for 10 minutes. A solution of the free base of 1-azabicyclo[3.2.1]octane-5-methanamine (0.85 g, 6.0 mmol) in anhydrous tetrahydrofuran (5 mL) was added, and the mixture was stirred at room temperature for 18 hours and at 50° C. for one hour. The mixture was concentrated in vacuo and partitioned between toluene (100 mL) containing a little 2-propanol and saturated sodium carbonate (50 mL). The organic layer was separated and the aqueous solution was extracted with toluene/2-propanol (50 mL). The combined organic solution was dried ($Na_2SO_4$), concentrated in vacuo, and filtered through alumina (eluted with 20% methanol/tetrahydrofuran). The concentrated filtrate was recrystallized from acetonitrile (2 crops) to afford 1.22 g (63%) of colorless solid; mp 159°-161° C.

Analysis: Calculated for $C_{17}H_{24}ClN_3O_2$: C, 60.44; H, 7.16; N, 12.44. Found: C, 60.02; H, 7.50; N, 12.31.

EXAMPLE 3

4-Amino-N-1-azabicyclo[3.2.1]oct-5-ylmethyl)-5-chloro-2-(2-methoxyethoxy)benzamide A solution of 4-amino-5-chloro-2-(2-methoxyethoxy)-benzoic acid (2.34 g, 9.5 mmol) in anhydrous tetrahydrofuran (12 mL) was treated with 1,1'-carbonyldiimidazole (1.62 g, 10.0 mmol), stirred for one hour, and degassed with a stream of nitrogen over 10 minutes. A solution of 1-azabicyclo[3.2.1]octane-5-methanamine (1.41 g, 10 mmol) in anhydrous tetrahydrofuran (10 mL) was added and the mixture was stirred for 18 hours at room temperature and for 5 hours at 50° C., then concentrated in vacuo. The residue was partitioned between 3 N sodium hydroxide (100 mL) and toluene (150 mL) containing a little 2-propanol, and the organic layer was separated. The aqueous solution was extracted with toluene (100 mL) containing a little 2-propanol, and the combined organic solution was washed with saturated sodium chloride, dried ($Na_2SO_4$), and concentrated in vacuo. The residue was filtered through alumina (eluted with 20% methanol/tetrahydrofuran), concentrated in vacuo and triturated from ether to afford 2.63 g (75%) of the title compound as a colorless solid; mp 97°–102° C.

For purification, a solution of the title compound (2.58 g, 7.0 mmol) in methanol (10 mL) was treated with a solution of fumaric acid (1.39 g, 7.0 mmol) in methanol (20 1 mL), the mixture stirred for 5 minutes and diluted with anhydrous ether (100 mL). The suspension was cooled (0° C.) and filtered. The residue was washed with ether and dried in vacuo to afford 2.93 g (86%) of the fumarate salt of the title compound; mp 173°–175° C.

Analysis: Calc. for $C_{18}H_{26}ClN_3O_3 \cdot C_4H_4O_4$: C, 54.60; H, 6.25; N, 8.68. Found: C, 54.30; H, 6.41; N, 8.68.

EXAMPLE 4

4-Amino-N-(1-azabicyclo[3.3.1]non-5-ylmethyl)-5-ylmethyl)-5-chloro-2-methoxybenzamide A suspension of 4-amino-5-chloro-2-methoxybenzoic acid (1.58 g, 7.8 mmol) in anhydrous tetrahydrofuran (8 mL) under nitrogen was treated with 1,1-carbonyldiimidazole (1.30 g, 8 mmol), stirred for one hour, and degassed with a stream of nitrogen for 15 minutes. A solution of 1-azabicyclo[3.2.1]nonane-5-methanamine (1.27 g, 8.2 mmol) in anhydrous tetrahydrofuran (8 mL) was added, and the mixture was stirred overnight (18 hours) and concentrated in vacuo. The residue was partitioned between 1.25 N sodium carbonate (75 mL) and methylene chloride (100 mL) containing a little isopropanol. The organic layer was separated and the aqueous solution was extracted with methylene chloride (50 mL). The combined organic solution was dried ($Na_2SO_4$), concentrated in vacuo, and the residue was triturated from cold ether. Recrystallization (2 crops) from acetonitrile containing a little methanol afforded 1.77 g (67%) of colorless crystals; m.p. 201.5°–203° C.

Analysis: Calculated for $C_{17}H_{24}ClN_3O_2$: C, 60.44; H, 7.16; N, 12.44. Found: C, 60.34; H, 7.26; N, 12.41.

EXAMPLE 5

N-(1-Azabicyclo[3.3.1]non-5-ylmethyl)-5-chloro-2-methoxy-4-(methylamino)benzamide A solution of 5-chloro-2-methoxy-4-(methylamino)-benzoic acid (1.08 g, 5 mmol) in anhydrous tetrahydrofuran (7 mL) under nitrogen was treated with 1,1'-carbonyldiimidazole (0.90 g, 5.5 mmol), stirred one hour, degassed under a stream of nitrogen for 10 minutes, and cooled (0° C.). A solution of 1-azabicyclo[3.3.1-nonane-5-methanamine (0.82 g, 5.3 mmol) in tetrahydrofuran (3 mL) was added dropwise, and stirring was continued at room temperature for 18 hours. The suspension was diluted with enough methanol to dissolve the solid, then the solution was filtered through a short column of alumina (eluted with 20% methanol/tetrahydrofuran). The filtrate was concentrated in vacuo, triturated from cold ether, and recrystallized from acetonitrile to afford 1.29 g (73%) of colorless crystals; mp 188°–190° C. (second phase), first phase melting point 175° C.

Analysis: Calculated for $C_{18}H_{26}ClN_3O_2$: C, 61.44; H, 7.45; N, 11.94. Found: C, 61.51; H, 7.60; N, 11.96.

EXAMPLE 6

4-Amino-N-(1-azabicyclo[3.3.1]non-5-ylmethyl)-5-chloro-2-(2-methoxyethoxy)benzamide A solution of 4-amino-5-chloro-2-(2-methoxyethoxy)-benzoic acid (2.09 g, 8.5 mmol) in anhydrous tetrahydrofuran (10 mL) under nitrogen was treated with 1,1'-carbonyldiimidazole (1.46 g, 9.0 mmol), stirred for one hour, degassed under a stream of nitrogen over 10 minutes, and cooled (0° C.). A solution of 1-azabicyclo[3.3.1]nonane-5-methanamine (1.36 g, 8.8 mmol) in tetrahydrofuran (5 mL) was added dropwise, and stirring was continued at room temperature for 18 hours. The solution was concentrated in vacuo and the residue was taken up in methylene chloride (100 mL) and washed with saturated sodium carbonate (50 mL). The organic solution was dried ($Na_2SO_4$), concentrated in vacuo, and passed through a short column of alumina (eluted with 5% methanol/methylene chloride). The filtrate was concentrated in vacuo and, at this point, appeared to be contaminated with some highly insoluble impurity. The residue was taken up in tetrahydrofuran and filtered, and the filtrate was concentrated in vacuo, triturated from cold ether, and recrystallized from acetonitrile (2 crops) to afford 1.59 g (49%) of colorless crystals; mp 154.0°–155.5° C.

Analysis: Calculated for $C_{19}H_{26}ClN_3O_3$; C, 59.76; H, 7.39; N, 11.00. Found: C, 59.52; H, 7.50, N, 10.99.

EXAMPLE 7

N-(1-Azabicyclo[3.3.1]non-5-ylmethyl)-1H-indole-3-carboxamide

A cooled (0° C.) suspension/solution of indole-3-carboxylic acid (0.92 g, 5.7 mmol) in anhydrous tetrahydrofuran (10 mL) was treated dropwise with thionyl chloride (0.72 g, 6.0 mmol), and the solution was refluxed for one hour and concentrated in vacuo. A cooled (0° C.) solution of 1-azabicyclo[3.3.1]nonane-5-methanamine (0.96 g, 6.2 mmol) and triethylamine (1.22 g, 12 mmol) in anhydrous tetrahydrofuran (5 mL) was treated with a solution of the above prepared acid chloride in anhydrous tetrahydrofuran (10 mL), and the mixture was stirred at room temperature for 15 hours, at 55° C. for one hour, and cooled (0° C.). Sodium methoxide/methanol (25%, 2.6 g, 12 mmol) was added, and the solution was stirred for one hour and passed through a column of alumina (eluted with 1:1 methanol/tetrahydrofuran). The filtrate was concentrated in vacuo and taken up in 2-propanol and filtered. Ether was added dropwise to the filtrate until no more precipitation was observed, and the suspension was cooled (0° C.), filtered, and the solid was collected and dried in vacuo to afford (after a second crop) 0.97 g (57%) of the title compound as a colorless solid; mp 139.0°–141.5° C.

For purification a solution of the solid in methanol (5 mL) was treated with a solution of fumaric acid (0.6 g, 5 mmol) in methanol (25 mL), and the mixture was stirred for 5 minutes and concentrated in vacuo. The residue was triturated from ether and recrystallized from ethanol/2-propanol to afford 0.82 g (52%) of the fumurate salt of the title compound as a colorless solid; mp. 203°–204° C.

Analysis: Calc. for $C_{18}H_{23}N_3O\cdot1.5C_4H_4O_4$: C, 61.14; H, 6.20; N, 8.91. Found: C, 61.06; H, 6.32; N, 8.89.

EXAMPLE 8

N-(1-Azabicyclo[3.3.1]non-5-ylmethyl)-1-methyl-1H-indole-3-carboxamide

A solution of 1-methyl-1-H-indole-3-carboxylic acid (1.53 g, 8.7 mmol) in anhydrous tetrahydrofuran (8 mL) under nitrogen was treated with 1.49 g (9.2 mmol) of 1,1'-carbonyldiimidazole (CDI) and stirred for 10 minutes. At this point a thick suspension formed, and anhydrous N,N-dimethylformamide (8 mL) was added. After an additional 45 minutes the solution was degassed under a stream of nitrogen over 10 minutes, then treated with a solution of 1-azabicyclo[3.3.1]nonane-5-methanamine (1.47 g, 9.5 mmol). After 18 hours at room temperature and six hours at 55°–60° C., no acid-CDI adduct was detected by TLC (5% methanol/methylene chloride on alumina), and the mixture was concentrated in vacuo. The residue was partitioned between 3N sodium hydroxide (50 mL) and toluene (100 mL) containing a little 2-propanol. The organic layer as separated and the aqueous solution was extracted with toluene (50 mL) containing some 2-propanol. The combined organic solution was dried ($Na_2SO_4$), concentrated in vacuo, and the residue filtered through alumina (eluted with 20% methanol/tetrahydrofuran). The filtrate was concentrated in vacuo and the residue triturated from ether/petroleum ethers (30°–60°) to give a solid, which was recrystallized from tetrahydrofuran/hexane to afford 2.06 g (76%) of colorless crystals; mp 145°–147° C.

Analysis: Calculated for $C_{19}H_{25}N_3O$: C, 73.28; H, 8.09; N, 13.49. Found: C, 73.28; H, 8.20; N, 13.43.

EXAMPLE 9

N-(1-Azabicyclo[3.3.1non-5-ylmethyl)-4-[(methylsulfonyl)aminol]benzamide

A solution/suspension of 4-[(methanesulfonyl)amino]benzoic acid (1.08 g, 5.0 mmol) in anhydrous 1:1 tetrahydrofuran/dimethylformamide (4 mL) was treated with 1,1'-carbonyldiimidazole (0.89 g, 5.5 mmol), stirred for one hour, then degassed over 15 minutes under a stream of nitrogen. A solution of 1-azabicyclo[3.3.1]nonane-5-methanamine (0.85 g, 5.5 mmol) in anhydrous tetrahydrofuran (4 mL) was added, and the mixture was stirred at room temperature for 18 hours and at 50° C. for three hours, then concentrated in vacuo. The residue was triturated from acetonitrile/ether, then dissolved in 3.2 tetrahydrofuran/methanol and filtered through a short column of alumina (eluted with 3:2 tetrahydrofuran/methanol). The filtrate was concentrated in vacuo and recrystallized (2 crops) from 2-propanol/ether to afford 0.61 g (32%) of the sesquihydrate of the title compound as a voluminous colorless solid; mp 137°–139° C. (foam).

Analysis: Calc. for $C_{17}H_{25}N_3O_3S\cdot1.5H_2O$: C, 53.95; H, 7.46; N, 11.10. Found: C, 54.14; H, 7.35; N, 10.49.

EXAMPLE 10

4-Amino-5-chloro-2-methoxybenzoic acid 1-azabicyclo[3.2.1]oct-5-ylmethyl ester

A solution of 4-amino-5-chloro-2-methoxybenzoic acid (1.62 g, 8.0 mmol) in anhydrous tetrahydrofuran (10 mL) under nitrogen was treated with 1,1'-carbonyldiimidazole (1.38 g, 8.5 mmol), stirred one hour, and degassed under a stream of nitrogen over 10 minutes. Meanwhile, a cooled (−10° C.) solution of 1-azabicyclo[3.2.1]octane-5-methanol (1.20 g, 8.5 mmol) in anhydrous tetrahydrofuran (10 mL) under nitrogen was treated (via syringe) with 2.50 N n-butyllithium/hexane (8.25 mmol), stirred for 30 minutes, concentrated in vacuo, and taken up in anhydrous tetrahydrofuran (10 mL) under nitrogen. The above degassed solution was transferred into this solution by syringe, and the mixture was stirred at room temperature for 65 hours and at 50° C. for one hour, then concentrated in vacuo. The residue was partitioned between toluene (100 mL) containing a little 2-propanol and saturated aqueous sodium carbonate (50 mL), and the organic layer was separated. The aqueous solution was extracted with toluene (2×50 mL) containing a little 2-propanol, and the combined organic solution was dried ($Na_2SO_4$) and concentrated in vacuo. The residue was filtered through alumina (eluted with 2% methanol/tetrahydrofuran, then with 35% methanol/tetrahydrofuran to collect product),and the filtrate was concentrated in vacuo and triturated from cold ether. Recrystallization from ethyl acetate/hexane afforded 1.23 g (47%) of a colorless solid; mp 131°–133° C.

Analysis: Calculated for $C_{16}H_{21}ClN_2O_3$: C, 59.17; H, 6.52; N, 8.62. Found: C, 59.13; H, 6.72; N, 8.64.

EXAMPLE 11

1H-Indole-3-carboxylic acid 1-azabicyclo[3.2.1]oct-5-ylmethyl ester

A solution of indole-3-carboxylic acid (1.45 g, 9 mmol) in anhydrous tetrahydrofuran (10 mL) under nitrogen was treated with 1,1'-carbonyldiimidazole (1.53 g, 9.4 mmol), stirred for one hour, and degassed with a stream of nitrogen over 10 minutes. Meanwhile, a cooled (−10° C.) solution of 1-azabicyclo[3.2.1]octane-5methanol (1.42 g, 10 mmol) in anhydrous tetrahydrofuran (10 mL) under nitrogen was treated (via syringe) with 2.5N n-butyllithium/hexane (9.7 mmol), stirred for 30 minutes, concentrated in vacuo, and taken up in anhydrous tetrahydrofuran (10 mL) under nitrogen. The acid 1,1'-carbonyldiimidazole adduct (suspension) was transferred into this solution, and the mixture was stirred overnight (18 hors) and concentrated in vacuo. The residue was partitioned between methylene chloride (100 mL) containing a little 2-propanol and saturated aqueous sodium carbonate (50 mL), and the organic layer was separated. The aqueous solution was extracted with methylene chloride (2×50 mL), and the combined organic solution was dried ($Na_2SO_4$), concentrated in vacuo and filtered through alumina (eluted with 5% methanol/methylene chloride). The concentrated filtrate was recrystallized from acetonitrile (2 crops) to afford 1.34 g (52%) of colorless solid; mp 183.5°–185.0° C.

Analysis: Calculated for $C_{17}H_{20}N_2O_2$: C, 71.81; H, 7.09; N, 9.85. Found: C, 71.53; H, 7.16; N, 9.98.

EXAMPLE 12

1-Methyl-1H-indole-3-carboxylic acid 1-azabicyclo[3.2.1]oct-5-ylmethyl ester

A solution of 1-methyl-1H-indole-3-carboxylic acid (1.75 g, 10 mmol) in anhydrous tetrahydrofuran (10 mL) under nitrogen was treated with 1,1'-carbonyldiimidazole (1.79 g, 11 mmol), stirred for one hour, and degassed under a stream of nitrogen over 10 minutes. Meanwhile a cooled (−10° C.) solution of 1-azabicyclo[3.2.1]octane-5-methanol (1.55 g, 11 mmol) in anhydrous tetrahydrofuran (10 mL) under nitrogen was treated (via syringe) with 2.5 N n-butyllithium/hexane (10.5 mmol), stirred for 30 minutes, concentrated in vacuo, and taken up in anhydrous tetrahydrofuran (10 mL) under nitrogen. The suspension of the acid/1,1'-carbonyldiimidazole adduct was transferred into this solution, and the mixture was stirred 18 hours at room temperature and 4 hours at 55° C., and concentrated in vacuo. The residue was partitioned between toluene (150 mL) containing some 2-propanol and saturated aqueous sodium carbonate (100 mL). The organic layer was separated and the aqueous solution was extracted with toluene (2×100 mL) containing some 2-propanol. The combined organic solution was dried ($Na_2SO_4$), concentrated in vacuo, and filtered through alumina (eluted with 20% methanol/tetrahydrofuran). The filtrate was concentrated in vacuo, triturated with petroleum ethers (30°-60°), and recrystallized from ether/petroleum ethers (2 crops) to afford 1.72 g (58%) of colorless solid; mp 94.5°-96.5° C.

Analysis: Calculated for $C_{19}H_{22}N_2O_2$: C, 72.46; H, 7.43; N, 9.39. Found: C, 72.32; H, 7.44; N, 9.33.

EXAMPLE 13

4-Amino-5-chloro-2-methoxybenzoic acid 1-azabicyclo[3.3.1]non-5-ylmethyl ester

A solution of 4-amino-5-chloro-2-methoxybenzoic acid (2.02 g, 10 mmol) in anhydrous tetrahydrofuran (10 mL) under nitrogen was treated with 1,1'-carbonyldiimidazole (1.70 g, 10.5 mmol), stirred for one hour, then degassed with a stream of nitrogen over 10 minutes. Meanwhile, a cooled (−10° C.) solution of 1-azabicyclo[3.3.1]nonane-5-methanol (1.71 g, 11 mmol) in anhydrous tetrahydrofuran (10 mL) under nitrogen was treated (via syringe) with 2.5N n-butyllithium/hexane (10.7 mmol), stirred for 30 minutes, concentrated in vacuo, and taken up in anhydrous tetrahydrofuran (10 mL) under nitrogen. The above prepared suspension was transferred into this solution, and the mixture was stirred overnight (18 hours) and concentrated in vacuo. The residue was partitioned between methylene chloride (100 mL) containing a little 2-propanol and saturated aqueous sodium carbonate (50 mL), and the organic layer was separated. The aqueous solution was extracted with methylene chloride (2×50 mL), and the combined organic solution was dried ($Na_2SO_4$), concentrated in vacuo and recrystallized from acetonitrile (2 crops) to afford 1.94 g (57%) of pale yellow solid; mp 152.5°-154.5° C.

Analysis: Calculated for $C_{17}H_{23}ClN_2O_3$: C, 60.26; H, 6.84; N, 8.27. Found: C, 60.02; H, 6.90; N, 8.15.

EXAMPLE 14

1H-Indole-3-carboxylic acid 1-azabicyclo[3.3.1]non-5-ylmethyl ester

A solution of indole-3-carboxylic acid (1.62 g, 10 mmol) in anhydrous tetrahydrofuran (10 mL) under nitrogen was treated with 1,1'-carbonyldiimidazole (1.70 g, 10.5 mmol),stirred for one hour, and degassed with a stream of nitrogen for 10 minutes giving a suspension. Meanwhile, a cooled (−10° C.) solution of 1-azabicyclo[3.3.1]nonane-5-methanol (1.71 g, 11 mmol) in anhydrous tetrahydrofuran (10 mL) under nitrogen was treated (via syringe) with 2.5 N n-butyllithium/hexane (10.7 mmol), stirred for 30 minutes, concentrated in vacuo, and taken up in anhydrous tetrahydrofuran (10 mL) under nitrogen. The 1,1'-carbonyldiimidazole adduct suspension was transferred into this solution, and the mixture was stirred overnight (18 hours) and concentrated in vacuo. The residue was partitioned between methylene chloride (100 mL) containing a little isopropanol and saturated sodium carbonate (50 mL), and the organic layer was separated. The aqueous solution was dried ($Na_2SO_4$), concentrated in vacuo, and filtered through alumina (eluted with 7% methanol/methylene chloride). The filtrated was concentrated in vacuo and the residue was triturated from cold ether and recrystallized from acetonitrile (2 crops) to afford 1.79 g (60% ) of colorless crystals; m.p. 207°-209° C.

Analysis: Calculated for $C_{18}H_{22}N_2O_2$: C, 72.46; H, 7.43; N, 9.39. Found: C, 71.98; H, 7.48; N, 9.59.

EXAMPLE 15

1-Methyl-1H-indazole-3-carboxylic acid 1-azabicyclo[3.2.1]oct-5-ylmethyl ester

A cooled (0° C.) solution of 1-azabicyclo[3.2.1]oct-5-ylmethanol (1.70 g, 12 mmol) in anhydrous tetrahydrofuran (15 mL) under nitrogen was treated (via syringe) with 2.45N n-butyllithium/hexane (12 mmol), then stirred at room temperature for thirty minutes and concentrated in vacuo to remove all hexane. Anhydrous tetrahydrofuran (15 mL) was added, followed by 3-(3H-imidazol-1-ylcarbonyl)-1-methyl-1H-indazole (2.49 g, 11 mmol), and the mixture was stirred under nitrogen at room temperature for 18 hours, then at 60° C. for three hours, and concentrated in vacuo. The residue was partitioned between 1.0N sodium carbonate (75 mL) and toluene (125 mL) containing some 2-propanol, and the organic layer was set aside. The aqueous solution was extracted with toluene (2×50 mL) containing some 2-propanol, and the combined organic solution was rinsed with water to remove imidazole, then dried azeotropically with toluene. The residue was filtered through alumina (eluted with 15% methanol/tetrahydrofuran), concentrated in vacuo, and triturated from ether/petroleum ethers (30°-60°), then recrystallized from ether/petroleum ethers (30°-60°) to afford 1.75 g (53%) of the product as a colorless solid; mp. 93°-95° C.

Analysis: Calculated for $C_{17}H_{21}N_3O_2$: C, 68.21; H, 7.07; N, 14.04. Found: C, 68.15; H, 7.12; N, 14.10.

EXAMPLE 16

4-Amino-N-(1-azabicyclo[3.2.1]oct-5-ylmethyl)-5-chloro-2-[2-(diethylamino)-2-oxoethoxy]benzamide Following the procedure of Example 1 the title compound is prepared from 4-amino-5-chloro-2-[2-(diethylamino)-2-oxoethoxy]benzoic acid and 1-azabicyclo[3.2.1]octane-5-methanamine.

EXAMPLE 17

4-Amino-N-(1-azabicyclo[3.2.1]oct-5-ylmethyl)-5-chloro-2-(2-propenyloxy)benzamide Following the procedure of Example 1, the title compound is prepared from 4-amino-5-chloro-2-(2-propenyloxy)benzoic acid and 1-azabicyclo[3.2.1]octan-5-methanamine.

EXAMPLE 18

4-Amino-N-(1-azabicyclo[3.3.1]nonan-5-ylmethyl)-5-chloro-2-[2-(methanylthio)ethoxy]benzamide Following the procedure of Example 1 the title compound is prepared from 4-amino-5-chloro-2-[2-(methylthio)ethoxy]benzoic acid and 1-azabicyclo[3.3.1]nonan-5-methanamine.

EXAMPLE 19

4-Amino-N-(1-azabicyclo[3.3.1]nonan-5-ylmethyl)-5-chloro-2-[2-(methylsulfonyl)ethoxy]benzamide A solution of the compound of Example 18 (6.5 mmol) in 75 mL of a 5:1 15% sulfuric acid/methanol mixture is treated with sodium perborate tetrahydrate (16 mmol) and the mixture is maintained at room temperature for 30 minutes. The acidic solution is basified with 3N sodium hydroxide solution, saturated with sodium chloride and extracted with methylene chloride to obtain the title compound.

PHARMACOLOGY METHODS AND PHARMACEUTICAL FORMULATIONS

A. Effect of Invention compounds on Cisplatin-induced Emesis in Dogs

The procedure used to test compounds of the present invention for antiemetic properties is a modification of the method of Gylys et al., Res. Commun. Chem. Pathol. Pharm. 23, 61(1979).

Adult, mongrel unfasted dogs of both sexes are randomly assigned into treatment groups, with each treatment group consisting of four dogs. On the dosing day all dogs are given cisplatin, 3.0 mg/kg, intravenously. Sixty minutes later, the dogs in the control treatment group are given deionized water, 0.1 mL/kg intravenously and dogs receiving test compounds are given the test compound in solution (1 mg/kg, IV). All doses are administered as a solution by means of a syringe and needle, and each dog's emetic episodes are recorded for 5 hours after the administration of cisplatin.

B. Effect of Invention compounds on Gastric Emptying of a Test Meal in Fasted Rats The procedure used to test compounds of the present invention for gastric motility enhancing activity is that of Droppleman et al., J. Pharmacol. Methods, 4, 277 (1980).

Each animal is dosed intraperitoneally (9 or 10 mg/kg) with a test compound or control. After 30 minutes each animal is given 3 mL of a methylcellulose-based test meal formulation. Sixty minutes after administration of the test meal, each animal is sacrificed by cervical dislocation, and the stomach is removed and weighed. The stomach is cut open, rinsed and dried, and reweighed. This difference between the full and empty weights (amount of meal remaining in stomach) is substrated from the weight of the original test meal to determine the meal amount emptied from the stomach during the test period.

C. Anxiolytic Test

Exploratory Light/Dark (mice)

This method has been described by Young and Johnson (1988) and is a modification of the procedure described by Costall and Naylor (1988). A two compartment light-dark activity monitoring device (Digiscan Model RXZYZCM16, Omnitech Electronics, Inc., Columbus, Ohio) issued. A 90W light source located 30 cm above the box provides light to the lit portion of the apparatus. Behavioral testing is conducted in a sound-attenuated, darkened room illuminated with red light (25W red bulb) only.

Each animal (mouse) receives a dose or doses of either the test, reference, or control article. The animal is placed at the center of the illuminated area and the behavioral activity tallied over a 5 minutes period by use of the Digiscan analyzer. Behavioral variables recorded included: the time spent in the lit and dark areas, the number of rearings in the lit and dark areas, the number of locomotor activity counts in the lit and dark areas, the number of transitions between the light and dark and lit areas, the latency to make the first transition from the lit area to the dark area, rearing time in the lit and dark areas, locomotor time in the lit and dark areas, and resting time in the lit and dark areas. Appropriate statistical analyses from each measure are performed. Significant increases in one or more of the parameters associated with behavior of the animals in the lit area versus behavior in the dark area correspond to active non-sedating anxiolytic compounds.

The compound of example 12 at 10 mg/kg IP caused a significant increase in the time spent in the lit area (58%) as compared with the controls (30%).

References

Young, R., Johnson, D. N., Soc. Neurosci. Abs. 1988, 14, 207.

Costall, B. Naylor, R., Brit. J. Pharmacol. 1988, 93, 985-993.

D. Antipsychotic Activity Test

The dopamine hypothesis of schizophrenia attributes some of the symptoms of this illness to a raised mesolimbic dopamine function. In order to mimic the discrete nature of this disturbance in experimental animals, stereotaxic surgery is used to aim dropamine or amphetamine at a discrete mesolimbic nucleus to produce hyperactivity. Test compounds are evaluated for their ability to block this response.

For example, the use of (+)-amphetamine injected intracerebrally in to the rate nucleus accumbens increases psychomotor drive which is measured as hyperactivity. Previous studies have shown that this response to amphetamine is selectively blocked by neuroleptic agents or agents having antischizophrenic potential.

Rats are subjected to standard stereotaxic techniques for the implantation of chronically indwelling bilateral guide cannulae for subsequent injections at the center of the nucleus accumbens. Immediately after (+)-amphetamine injection, rates are placed in activity chambers containing infrared photocell units. Hyperactivity is measured as the numbers of interruptions of the photocell beams per unit time.

For dopamine infusion, Alset osmotic mini pumps are implanted into the rats, with subcutaneous polyethylene tubing connecting the pump to the chronically implanted guide cannulae. Over a 13 day period, dopamine in continuously infused into the nucleus accumbens. For an appropriate period of time each day, the locomotor activity is monitored in activity chambers as described above.

Ability of known antischizophrenic agents to antagonize hyperactivity caused by intra-accumbens injection of amphetamine or dopamine is established using fluphenazine and sulpiride. These agents are administrated peripherally or intra-cerebrally prior to administration of amphetamine or daily to those animals with continuous dopamine infusion. Similarly, test compounds are evaluated for their ability to block the hyperactivity produced by amphetamine or dopamine.

Based on profiles of similar compounds in standard pharmacological tests, Formula I compounds of the present invention can exhibit antipsychotic activity in rats under test conditions.

E. Improvement of Cognitive Function Activity Test

This test allows the measurement of cognitive function in rats. The animals are trained to respond to a single path in a T-maze to obtain a rearward (food). The environment then is altered to present a choice of two paths, only one of which leads to the reward. Performance is evaluated by the determination of ratio of correct to incorrect responses and latency so reward for all test paradigms. In addition, performance of rats in the T-maze can be significantly impaired by scopolamine, and compounds are evaluated for their ability to reverse this response.

Male rats, maintained at 85% of normal body weight, are used. The T-maze is constructed of wood and elevated 30 cm from the ground with side arms measuring 60 cm × 10 cm and with start arm measuring 80 cm × 10 cm. A small metal cup, placed towards the end of each side arm, holds the reward pellets. T-maze training consists of paired trails, the first being "forced" in that one side arm is blocked with a wooden barrier while the other is baited. The second is a "choice" trial in which reward pellets are placed in the side arm opposite to that reinforced on the first trial of the pair. A correct choice is recorded when the rat enters the side arm containing the food on the choice trail. The ratio of correct/incorrect choices, and latency to reward are recorded for both forced and choice trials.

The performance of rats in the T-maze can be significantly impaired by the amnestic agent scopolamine. Test compounds are evaluated as antagonists of the disruptive action of scopolamine. Active compounds are those which block the cognitive deficit produced by scopolamine.

Based on profiles of similar compounds in standard pharmacological tests, Formula I compounds of the present invention can exhibit cognition function improvement activity in rates under test conditions.

F. Antagonism of the von Bezold-Jarisch Reflex

The compounds are evaluated for antagonism of the von Bezold-Jarisch reflex evoked by 5-HT (serotonin) in anaesthetized rats according to the method described in European patent Application 200-444 (Beecham Group).

Male rats (250-350 g) are anaesthetized with urethane (1.25 g/kg intraperitoneally), and blood pressure and heart rate are recorded as described by Fozard J. R. et al., J. Cardiovasc. Pharmacol. 2, 229-245 (1980). A submaximal dose of 5-HT (usually 6 m/kg) is given repeatedly by the intravenous route and changes in heart rate quantified. Compounds are given intravenously and the inhibition of the 5-HT evoked response is measured. In addition, the concentration required to reduce the 5-HT evoked response to 50% of the control response ($ED_{50}$) can be determined.

Formula I compounds of the present invention exhibit selective 5-HT antagonist activity, and therefore are useful for alleviation of migraine, cluster headache and trigeminal neuralgia symptoms in warm blooded animals.

G. Measurement of Cellular Electrophysiologic Effects in Canine Purkinje Fibers In Vitro Dogs (12-18 kg) were anesthetized with sodium pentobarbital (30 mg/kg IV).The heart of each dog was rapidly removed through a right lateral thoracotomy and placed in a chilled, oxygenated Tyrode's solution. Purkinje fibers from the right and left ventricles were excised and mounted in a Lucite chamber. The tissue was superfused at a rate of 10-15 mL/min with Tyrode's solution. The temperature of the superfused Tyrode's was maintained at 37° C. and gassed with 95% oxygen-5% carbon dioxide mixture.

The Purkinje fibers were stiumulated (paced at cycle length of 400 to 1000 msec) with a silver bipolar wire electrode placed on the surface of the tissue. Transmembrane action potentials were recorded with a glass capillary microelectrodes filled with 3M KCl. The action potentials were displayed on a Tectronix 5113 oscilloscope. The measurements derived from the action potential were Vmax (upstroke velocity), APD50 (action potential duration at 50% repolarization), and APD90 (action potentional duration at 90% repolarization) as previously described (Bigger and Mandel, 1970; Wu and Hoffman, 1987). Test compounds were added to the reservoir of Tyrode's solution to concentrations of 10 and 100 uM. Measurements of the action potential parameters were recorded after 20 min of test drug exposure. These measurements were compared to those obtained prior to the test compound. Changes in the action potential measurements produced by the test compound were analyzed for statistical significance using a paired-t test. A minimum of 3 tissues were used for each test compound.

The compound of Example 9 increased the action potential at 90% repolarization (APD90) by 8.5 ($\pm$5.0) % at $10^{-4}$M.

References

Bigger, J. T. and Mandel, W. J. Effects of lidocaine on the electrophysiologic properties of ventricular muscle and Purkinje fibers, J. CLIN. INVEST. Vol 49: 63-77 (1970).

Wu, K. M. and Hoffman, B. F. Effect of procainamide and N-acetylprocainamide on atrial flutter, studies in vivo and in vitro. CIRCULATION Vol 76:1397-1408 (1987).

TABLE II

| | Pharmacology Data | | |
|---|---|---|---|
| Example | Gastric Emptying[1] | Antiemetic[2] | Antiserotonin[3] |
| 1 | +47 (10) | −76 | |
| 2 | +62 (09) | −63 | |
| 3 | −31 (10) | −51 | −74 |
| 4 | −31 (10) | −62 | −32 |
| 5 | +58 (09) | −71 | |
| 6 | | | −30 |
| 8 | | −49 | |
| 10 | +47 (10) | −82 | −82 |
| 11 | | −85 | −86 |
| 12 | | | −81 |
| 13 | +41 (09) | −50 | −23 |
| 14 | +10 (09) | | −0.3 |
| 15 | −31 (10) | −93 | −72 |

[1] % change in gastric emptying of test meal in rats (dose, mg/kg IP)
[2] % change in emetic episodes in dogs at 1 mg/kg IV induced by cisplatin
[3] Von Bezold-Jarisch reflex- % change in serotonin-induced bradycardia at 0.0316 mg/kg IV in anesthesized rats.

Generally, the method of controlling emesis and gastric emptying, treating anxiety and disorders due to serotonin imbalance such as migraine, trigeminal neuralgia, psychosis, cognitive dysfunction, and cardiac arrhythmia in accordance with this invention comprises administering internally to warm-blooded animals, including human beings, a therapeutically effective amount of a compound of Formula I or a pharmaceutically acceptable salt in a wide variety of pharmaceutical forms well known in the art, preferably with a non-toxic pharmaceutical carrier. The active agent is administered orally, subcutaneously, intravenously, or intramuscularly and, if necessary, in repeated dosages until satisfactory response is obtained. Compositions for oral administration can take the form of elixirs, capsules, tablets, or coated tablets containing carriers conveniently used in the pharmaceutical art. Exemplary of solid carriers including tableting and capsulating excipients are lactose, sucrose, potato and maize starches, talc, gelatin, agar, pectin or acacia, stearic and silicic acids, magnesium stearate, terra alba and polyvinyl pyrrolidone. For parenteral administration, the carrier or excipient can be comprised of a sterile parenterally acceptable liquid, e.g., water or arachis oil contained in ampoules.

To facilitate gastric emptying a dosage of from 1 to 100 mg/kg, preferably 1-10 mg/kg, is contemplated. To inhibit emesis due tothe administration of platinum and non-platinum anticancer drugs or radiation, a dosage of 1-10 mg/kg, preferably 0.1-10.0 mg/kg is contemplated. Co-formulation of a Formula I compound and an anticancer drug is within the purview of this invention. To ameliorate or inhibit the effects of a serotonin imbalance, a dosage of 0.01-10.0 mg/kg may be used. To reduce anxiety, the effective amount of a Formula I compound is thought to be from 3-100 mg/kg, preferably 3-50 mg/kg of body weight.

In all of the above, it is only necessary that a suitable effective dosage be consistent with the dosage form employed. The exact individual dosages, as well as the daily dosages, will of course be determined according to standard medical principles under the direction of a physician or veterinarian.

The principles, preferred embodiments and modes of operation of the present invention have been described in the foregoing specification. The invention which is intended to be protected herein, however, is not to be construed as limited to the particular forms disclosed, since these are to be regarded as illustrative rather than restrictive. Variations and changes may be made by those skilled in the art without departing from the spirit of the invention, and it is therefore understood that the invention is to be limited only by the scope of the appended claims.

What we claim is:

1. A compound of the formula:

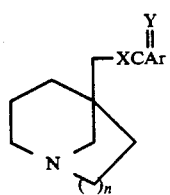

wherein
n is 1 or 2,
X is NH or O
Y is O or S and
Ar is

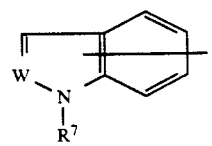

wherein
W is CH or N, and
$R^7$ is H or $C_1$-$C_4$ allyl, the stereoisomers;
the N-oxide,
or a pharmaceutically acceptable salt thereof.

2. A compound according to claim 1 which is selected from:
N-(1-Azabicyclo[3.3.1]non-5-ylmethyl)-1H-indole-3-carboxamide,
N-(1-Azabicyclo[3.3.1]non-5-ylmethyl)-1-methyl-1H-indole-3-carboxamide,
1H-indole-3-carboxylic acid 1-azabicyclo[3.2.1-oct-5-ylmethyl ester,
1-Methyl-1H-indole-3-carboxylic acid 1-azabicyclo[3.2.1]oct-5-ylmethyl ester.
1H-Indole-3-carboxylic acid 1-azabicyclo[3.3.1]non-5-ylmethyl ester, or
1-Methyl-1H-indazole-3carboxylic acid 1-azabicyclo[3.2.1]oct-5ylmethyl ester.

3. A method of treating impaired gastric motility in a warm-blooded animal in need thereof by internal administration of a therapeutically effective amount of a compound according to the formula:

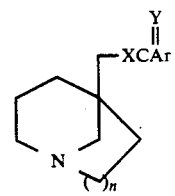

wherein
n is 1 or 2,
X is NH or O,
Y is O or S and
Ar is

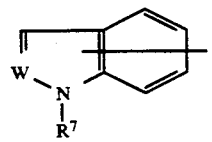

wherein
W is CH or N, and
$R^7$ is H or $C_1$-$C_4$ alkyl, the stereoisomers,
the N-oxide,
or a pharmaceutically acceptable salt thereof.

4. A method of treating emesis in a warm-blooded animal in need thereof by internal administration of a therapeutically effective amount of a compound according to the formula:

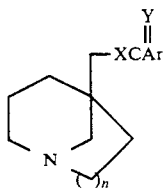

wherein
n is 1 or 2,
X is NH or O,
Y is O or S and
Ar is

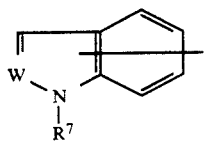

wherein
W is CH or N, and
R⁷ is H or $C_1$-$C_4$ alkyl, the stereoisomers,
the N-oxide,
or a pharmaceutically acceptable salt thereof.

5. A method of treating anxiety in a warm-blooded animals in need thereof by internal administration of a therapeutically effective amount of a compound according to the formula:

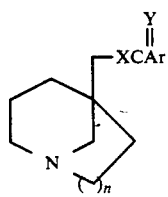

wherein
n is 1 or 2,
X is NH or O,
Y is O or S and
Ar is

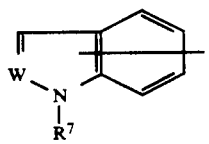

wherein
W is CH or N, and
R⁷ is H or $C_1$-$C_4$ alkyl, the stereoisomers,
the N-oxide,
or a pharmaceutically acceptable salt thereof.

6. A method of treating cardiac arrhythmias in a warm-blooded animal in need thereof by internal administration of a therapeutically effective amount of a compounds according to the formula:

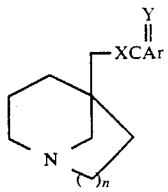

wherein
n is 1 or 2,
X is NH or O,
Y is O or S and
Ar is

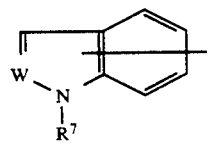

wherein
W is CH or N, and
R⁷ is H or $C_1$-$C_4$ alkyl; the stereoisomers,
the N-oxide,
or a pharmaceutically acceptable salt thereof.

7. A method of treating disorders due to serotonin imbalance in a warm-blooded animal in need thereof by internal administration of a therapeutically effective amount of a compound according to the formula:

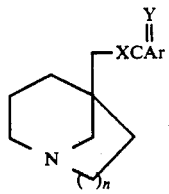

wherein
n is 1 or 2,
X is NH or O,
Y is O or S and
Ar is

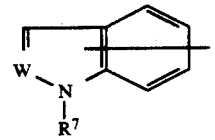

wherein
W is CH or N, and
R⁷ is H or $C_1$-$C_4$ alkyl, the stereoisomers,
the N-oxide,
or a pharmaceutically acceptable salt thereof.

8. A pharmaceutical composition for the treatment of warm-blooded animals for impaired gastric motility, emesis, anxiety, cardiac arrhythmias or disorders due to serotonin imbalance comprised of:

a therapeutically effective amount of a compound according to the formula:

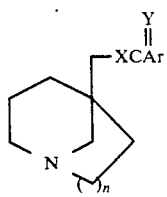
wherein
n is 1 or 2,
X is NH or O,
Y is O or S and
Ar is
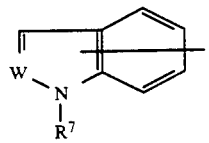
wherein
W is CH or N, and
$R^7$ is H or $C_1$–$C_4$ alkyl, the stereoisomers,
the N-oxide,
or a pharmaceutically acceptable salt thereof, and
b. a pharmaceutical carrier thereof.
* * * * *